United States Patent [19]
Pais et al.

[11] Patent Number: 4,482,550
[45] Date of Patent: Nov. 13, 1984

[54] FODDER AND FODDER ADDITIVES PROMOTING THE WEIGHT INCREASE OF DOMESTIC ANIMALS AND A PROCESS FOR THE USE THEREOF

[76] Inventors: Istvan Pais, 8/b, Frakno u., 1115 Budapest; Magda Feher nee Ravasz, 27, Vercse u., 1124 Budapest; Balint Nagy, 5, Ervin u., 1026 Budapest; Jozsef Bokori, 31/b, Damjanics u., 1071 Budapest; Zoltan Szabo, 19, Dozsa Gyorgy ut, 1038 Budapest, all of Hungary

[21] Appl. No.: 404,921

[22] Filed: Aug. 3, 1982

[30] Foreign Application Priority Data

Aug. 4, 1981 [HU] Hungary .............................. 2261/81

[51] Int. Cl.$^3$ ............................................. A61K 31/55
[52] U.S. Cl. .................................... 424/245; 424/131; 426/2
[58] Field of Search ...................... 426/2, 74, 623, 630, 426/635, 807; 424/131, 245, 280, 287

[56] References Cited

U.S. PATENT DOCUMENTS 2,907,658  10/1959  Luther ................................. 424/280
3,076,834   2/1963  Norton ............................ 424/245 X
3,224,935  12/1965  Burt ..................................... 424/287
4,020,158   4/1977  Ashmead et al. ............... 424/287 X
4,351,735   9/1982  Buddemeyer et al. ........... 426/74 X

OTHER PUBLICATIONS

Marstrand "Copper and Titanium Complexes with Ascorbic Acid," Chemical Abstracts, vol. 89, p. 403, Abstract No. 135868x.

Primary Examiner—R. B. Penland
Attorney, Agent, or Firm—Young & Thompson

[57] ABSTRACT

Fodder and fodder additives promoting the weight increase of domestic animals, and a process for the use thereof. The fodder and fodder additives of the invention contain stable complexes of titanium formed with ascorbic acid, o-dihydroxybenzene, dihydroxy naphthalene disulfonic acids, hydroxy carboxylic acids or polyhydroxy carboxylic acids or the salts thereof, preferably in a quantity of 0.001–6.00 percent by weight of the whole. Optionally, compounds exerting a preserving effect, preferably in a quantity of 0.01–2.0 percent by weight of the titanium complex, can be added, besides the usual components and additives of the fodder. The fodder and fodder additives of the invention promote the weight increase of domestic animals and reduce the specific fodder consumption.

3 Claims, No Drawings

FODDER AND FODDER ADDITIVES PROMOTING THE WEIGHT INCREASE OF DOMESTIC ANIMALS AND A PROCESS FOR THE USE THEREOF

The invention relates to fodder and fodder additives promoting the weight increase of domestic animals as well as to a process for the use thereof.

All over the world agriculturalists are making significant efforts to produce more and more valuable food raw materials for the increasing world population. In the case of animal fodder—e.g. corn ensilage, lucerne meal, the hay of fodder-plants and so on—different supplementary substances are admixed which improve the utilization of the fodder and ensure that the domestic animals reach the desired weight for slaughter within the shortest possible time. These supplementary substances comprise vitamins, hormones, antibiotics and trace elements.

It has long been known that every living organism needs micronutrients, that is, trace elements, as well as macronutrients, for the undisturbed occurrence of the biochemical processes. The most important trace elements are iron, manganese, zinc, copper, molybdenum and iodine. The trace elements exert their activity first of all as components of enzymes or as activators thereof. A lack of trace elements can cause metabolic disorders; hence the trace elements are of great importance for animal feeding. Nowadays there are detailed tables available from which the recommended trace element content of the fodder for the individual kinds of domestic animals can be determined.

It is an object of the invention to provide simple and cheap fodder additives and fodder containing the same, which promote the weight increase of domestic animals.

It is another object of the invention to provide a process for the use of these fodders and fodder additives.

The invention is based on the recognition that the fodder utilization of domestic animals can be increased by the addition thereto of water-soluble titanium complexes.

As a result of research work of many years, it has been observed that titanium exerts an advantageous effect on the redoxy enzyme activity of domestic animals and thus on the biochemical processes taking place.

A further feature of the invention is the recognition that the stability of the water-soluble titanium chelates against oxidation and microorganisms can be increased by adding substances having a preserving effect. Therefore, the addition of compounds having a preserving effect to the fodder and fodder additives containing titanium complexes according to the invention is desirable if they are stored in a wet environment or under high atmospheric humidity.

Accordingly, the invention relates to fodder and fodder additives promoting the weight increase of domestic animals. It is characteristic of the fodder and fodder additives of the invention that they contain water-soluble, stable complexes of the titanium formed with ascorbic acid, o-dihydroxybenzene, dihydroxy naphthalene disulfonic acids, hydroxy carboxylic acids or polyhydroxy carboxylic acids or the salts thereof, in a quantity of 0.001–6.0 percent by weight of the whole, and optionally compounds exerting a preserving effect in a quantity of 0.01–2.0 percent by weight of the titanium chelate.

Accordingly, the fodder and fodder additives of the invention contain, besides the usual supplementary additives such as vitamins, hormones, antibiotics, conventional trace elements and so on, at least 0.001 percent by weight of the whole, of titanium agents in the form of stable complexes.

Taking into consideration that the quantity of titanium intake related to the weight of the body is suitably 1–10 mg/kg/day, the fodder and fodder additives of the invention contain preferably 0.005–0.20 percent by weight of titanium. A further increase of the titanium content does not cause a further increase in weight gain but it does not harm the animals.

As water-soluble stable titanium complexes preferably the compounds of titanium formed with ascorbic acid, o-phenolcarboxylic acids and dihydroxynaphthaline derivatives, e.g. with salicylic acid, p-amino-salicylic acid, 5-sulfosalicylic acid, pyrocatechol, or chromotropic acid can be used. The complex formed with ascorbic acid is particularly preferred.

As compounds having a preserving effect preferably sorbic acid, benzoic acid, salicylic acid, p-chlorobenzoic acid, propionic acid or the salts of these acids or hexamethylenetetramine can be used.

The effect promoting the weight increase of the domestic animals of the titanium complexes added to the fodder or fodder additives has been proven in numerous large-scale tests. It has been found that—if the desired effect is to be achieved—the titanium has to be ingested by the animal in water-soluble form and at a time when the animal is preferably still young (in mammals after delactation).

In feeding experiments it has been found that a significant weight increase and parallel to it a specific fodder saving can be attained due to the titanium complex added to the fodder. In the course of these experiments no veterinary problems, harmful clinical symptoms or pathological changes were observed.

In the course of the feeding experiments several series of tests were carried out in order to find out whether the complex-forming compound itself is responsible for the advantageous effect. In these series of experiments besides the control group a further group of animals was fed the fodder, with which no titanium but only a complexing agent was admixed. In individual cases in this group, too, a slight positive effect was observed which, however, could not be compared with the much greater positive effect of the titanium complex.

As the necessary quantity of titanium related to the live weight (1 to 10 mg/kg/day) is very small, the titanium complex has to be admixed with the fodder very uniformly. Suitably fodder lime, bone meal or the mineral substances usual as fodder supplements are used for the necessary dilutents.

The main advantage of the invention resides in the fact that it renders possible an increase of the weight gain of domestic animals and at the same time a reduction of the specific fodder requirement in a simple and cheap way and this is of extraordinary importance in the present situation of "protein hunger" all over the world.

The invention is further illustrated with the help of the following examples:

EXAMPLE 1

100 to 400 ml of titanium tetrachloride are added to 0.5 to 2.0 kg of solid ascorbic acid in small portions with constant stirring and evacuation of the formed hydrochloric acid gas. The slowly hardening product, a yellowish or rust-colored mass, is carefully homogenized in a grinder with nearly the same quantity of fodder lime. The obtained mixture is admixed with 100 to 1600 kg of commercial chicken fodder.

An experiment was carried out with the fodder obtained in this way, on 3×60 chickens chosen after a two-week prebreeding and it was repeated four times, that is in every group of 4×15 chickens. The 60 chickens of the first group got the usual fodder, the 60 chickens of the second group got fodder admixed with ascorbic acid and the 60 animals of the third group were fed fodder containing the titanium complex. After five weeks of feeding the weight of the chickens fed with the fodder containing the titanium complex was significantly higher by 5% than that of the control group. The results are summarized in Table 1.

TABLE 1

Results of Experiments Carried Out on Broiler Chickens

| Fodder | Weight of the Animals, g | | | Difference in Weight from the Control, g | Specific Fodder Consumption, kg |
|---|---|---|---|---|---|
| | 30th day | 41st day | 51st day | | |
| Normal, no additive | 560.3 | 1006.8 | 1327.5 | 0 | 2.89 |
| Chelating agent | 569.5 | 1010.2 | 1333.2 | 5.7 | 2.89 |
| Titanium chelate | 586.5 | 1042.2 | 1395.2 | 67.7 | 2.73 |

EXAMPLE 2

The mixture of Example 1 of a chelate complex and lime was admixed with duck fodder in a quantity corresponding to a titanium dose of 1-2 mg/kg/day. The feeding experiments were carried out on a group of hybrid ducks (house duck, wild duck). The weight of the 3×50 treated and the 3×50 animals serving as controls was determined weekly, and the specific fodder consumption per 1 kg of live weight was calculated. The results are summarized in Table 2.

TABLE 2

Results of Experiments Carried Out on Ducks (F-2 hybrids)

| | Average Weight, kg After | | | Fodder Consumption kg/kg Live Weight |
|---|---|---|---|---|
| | 4 | 5 | 6 Wks. | |
| Control | 0.82 | 0.94 | 1.12 | 3.59 |
| Treated | 0.84 | 1.03 | 1.22 | 3.21 |

EXAMPLE 3

Feeding experiments were carried out on 3-week-old geese in the course of which the animals got the titanium chelate in capsules. Every group (fed with normal fodder, with fodder containing a complexing agent and a titanium complex, respectively) consisted of 10 animals. After two weeks the weight of the test animals was determined and the specific fodder consumption was defined. As it is seen in Table 3, the advantageous effect is obvious in this case, too. Presumably the result would have been still better if the administration of the capsules had not caused a stress effect.

TABLE 3

Results of Experiments Carried Out on Geese

| Treatment | Weight, g | Difference in Weight from the Control, g | Specific Fodder Consumption, kg/kg Live Weight |
|---|---|---|---|
| Control | 3312 | 0 | 2.98 |
| Chelating agent | 3314 | +2 | 3.20 |
| Titanium complex | 3461 | +149 | 2.89 |

EXAMPLE 4

Feeding tests were carried out on female young pigs for more than four months, wherein 30 animals formed the control group and another 30 animals got fodder containing titanium chelate. The weight of the animals measured completely identically was determined. The average weights of the two groups are included in Table 4 (an average of 28 animals each because two animals of every group were removed in the course of the test).

TABLE 4

Feeding Test on Female Young Pigs

| | Average Weight Increase of an Animal, kg After | |
|---|---|---|
| Treatment | 5 | 8 Weeks |
| Control | 21.2 | 29.4 |
| Treated | 23.5 | 33.2 |

EXAMPLE 5

Feeding tests were carried out on lambs for more than two months. 50 of the male animals 70 days old formed the control group and 50 were fed with fodder containing titanium chelate. The average starting weight of the animals of the control group was 19.48 kg, that of the treated group 19.70 kg The animals of the test group ingested a quantity of chelate corresponding to 25 mg of titanium every day.

At the end of the test the average weight of the animals of the control group was 38.52 kg while that of the animals of the test group amounted to 41.52 kg. That means a 14.6% greater weight increase, which corresponds to a significant saving of fodder since the animals received identical quantities of fodder.

EXAMPLE 6

Feeding tests were carried out on 300 rabbits. 150 of which formed the control group and were fed with the usual rabbit fodder while the other 150 animals got titanium complex in a quantity of 2 mg/kg/day titanium admixed with the fodder. At the beginning of the test the average weight of the animals of the control group was 643 g, that of the animals of the test group 646 g. In the course of the experiment lasting 36 days, it could be observed that the animals of the test group had a better appetite. On the 36th day the animals were weighed. The average weight increase in the test group was 1006 g, but in the control group only 956 g, which corresponds to a difference of 5.2%. This is a significant result in intensive animal keeping.

EXAMPLE 7

A pig fattening test lasting 76 days was carried out wherein 134 pigs formed the control group and the same number of animals the test group fed with fodder containing titanium chelate. Table 5 shows the advantageous effect of the chelate complex.

TABLE 5

Results of Pig Fattening Test

| Treatment | Average Daily Weight Increase | | Specific Fodder Consumption |
|---|---|---|---|
| | g | % | |
| Control | 451.7 | 100 | 2.71 kg (100%) |
| Treated | 512.5 | 113.4 | 2.38 kg (87.8%) |

EXAMPLE 8

Feeding tests were carried out on sheep for two months wherein the control group consisted of 50 animals and another 50 animals were fed with fodder containing titanium chelate. At the end of this test the weight of the animals was determined and the specific fodder amount was calculated. The results are summarized in Table 6.

TABLE 6

Results of Feeding Tests Carried Out on Sheep

| Treatment | Average Daily Weight Increase | | Specific Fodder Consumption | |
|---|---|---|---|---|
| | g | % | kg | % |
| Control | 277.0 | 100 | 6.20 | 100 |
| Treated | 361.3 | 130.4 | 5.11 | 82.4 |

EXAMPLE 9

Feeding tests were carried out on 4×12 fatted calves. Twelve bull calves and 12 heifers were fed with fodder containing titanium chelate while the control groups consisting also of 12 bull calves and 12 heifers got normal fodder. At the end of the test the weight of the animals, the specific fodder consumption and the additional weight increase produced by the treatment (weight increase of the control=100%) were determined. The results are summarized in Table 7.

TABLE 7

Results of the Test Carried Out on Calves

| Treatment | Average Starting Weight, kg | Average Slaughter Weight, kg | Weight Increase % |
|---|---|---|---|
| Bull calves | | | |
| Control | 121.33 | 190.17 | 100 |
| Treated | 122.25 | 198.83 | 111.3 |
| Heifers | | | |
| Control | 125.83 | 169.75 | 100 |
| Treated | 125.33 | 175.25 | 113.7 |

What is claimed is:

1. A process for promoting the weight increase of domestic animals, comprising feeding to said animals fodder containing a small but effective amount of a water-soluble, stable complex of tetravalent titanium formed with ascorbic acid, said amount being effective to make said animals gain more weight than if fed a fodder that does not contain a said titanium complex.

2. A process as claimed in claim 1, in which said amount is 0.001-0.15 percent by weight of the whole.

3. A process as claimed in claim 1, in which the fodder contains, as a compound having a preserving effect, sorbic acid, benzoic acid, salicylic acid, p-chlorobenzoic acid or propionic acid or the salts of these acids or hexamethylenetetramine.

* * * * *